(12) United States Patent
Davis (10) Patent No.: US 7,876,884 B2
(45) Date of Patent: *Jan. 25, 2011

(54) CONCRETE RADIOGRAPHY

(75) Inventor: James Davis, Fallbrook, CA (US)

(73) Assignee: Davis Laboratories, Inc., Brea, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/540,696

(22) Filed: Aug. 13, 2009

(65) Prior Publication Data

US 2009/0304155 A1    Dec. 10, 2009

Related U.S. Application Data

(63) Continuation-in-part of application No. 12/136,245, filed on Jun. 10, 2008, now Pat. No. 7,602,884.

(51) Int. Cl.
*H05G 1/28* (2006.01)

(52) U.S. Cl. .................................. 378/162

(58) Field of Classification Search ............ 378/57, 378/62, 147, 149, 162

See application file for complete search history.

(56) References Cited

U.S. PATENT DOCUMENTS

| | | | | |
|---|---|---|---|---|
| 5,052,035 | A | * | 9/1991 | Krupnick ............... 378/163 |
| 5,285,785 | A | * | 2/1994 | Meyer ................. 600/426 |
| 5,299,254 | A | * | 3/1994 | Dancer et al. ........... 378/163 |
| 5,394,457 | A | * | 2/1995 | Leibinger et al. ........ 378/162 |
| 5,469,847 | A | * | 11/1995 | Zinreich et al. .......... 600/414 |
| 5,933,473 | A | * | 8/1999 | Kitaguchi et al. ......... 378/57 |
| 6,118,848 | A | * | 9/2000 | Reiffel ................ 378/65 |

* cited by examiner

*Primary Examiner*—Irakli Kiknadze
(74) *Attorney, Agent, or Firm*—James A. Italia; Italia IP (57) ABSTRACT

An improved way of using radiographic imagery to capture internal characteristics of a concrete structure, wherein radiographic film is placed on one side of the concrete structure and X-rays are transmitted towards the film from the other side. A target which is selectively radiographically impervious may be interposed to generate location or guidance indicia on the film. The target may itself be non-symmetric, such as being L-shaped, or alternatively or in addition, the location indicia may be non-symmetrically located on the target or alternatively, may be arrayed about the circumference of the target similar to numerals of a clock face. Imagery resulting from radiographic imagery may or may not display inclusions and other anomalies of the concrete structure.

20 Claims, 7 Drawing Sheets

CONCRETE RADIOGRAPHY

CROSS-REFERENCE TO RELATED APPLICATION

This application is a Continuation-in-Part of U.S. Non-Provisional application Ser. No. 12/136,245 filed Jun. 10, 2008, now U.S. Pat. No. 7,602,884 and claims the benefit of priority thereto.

FIELD OF THE INVENTION

The present invention relates to viewing into the interior of concrete structures, such as columns, and more particularly, relates to method and apparatus for using radiography to generate images of the interior of concrete structures.

BACKGROUND OF THE INVENTION

It is occasionally necessary to determine internal construction of concrete structures, such as location of inclusions and other anomalies within concrete structures such as concrete columns or slabs, or to confirm the absence of inclusions and anomalies. This situation may arise for example when contemplating core drilling or cutting through the concrete structure. It is highly desirable to avoid impinging upon inclusions, such as reinforcement bars (hereinafter referred to as rebar), conduits, post tensioning cables, and the like. It may also be desirable to discriminate among inclusions, where several inclusions are in relatively close proximity to one another.

Purposes exist other than avoiding disruption to necessary building elements. For example, it may be desirable to ascertain internal integrity of concrete structures or lack thereof, for example to produce evidence for litigation purposes even if no boring or cutting is to be performed.

SUMMARY OF THE INVENTION

The present invention uses radiography both to locate inclusions and other anomalies within concrete and also to confirm absence of inclusions and other anomalies. According to one aspect of the invention, a target for imposing location indicia on the final radiographic image may be employed. For example, the target may comprise a metallic plate having radiopaque letters and numbers formed therein. X-rays passing the target will generate corresponding letters and numbers in the radiographic film which is struck by the X-ray. Of course, the entire target may be radiopaque, with the letters, numbers, or other indicia formed as radiographically permeable material to the same effect. Regardless of its precise nature, and whether it is formed as a positive image or a negative image, the indicia may be employed to determine distances and to enable other indexing or referencing to locate an inclusion identified within the concrete structure being radiographed and to identify locations on concrete not bearing inclusions and other anomalies.

The target may be specially configured to cooperate with irregularly shaped features of the concrete structure. Illustratively, the target may be L-shaped so that it can be placed snugly against a square or rectangular concrete structure. Alternatively, the target may have location indicia which is asymmetrically or irregularly located on the target. For example, a target placed in the inside corner of concrete walls meeting at a right angle may have indicia specially located so that the internal features of the concrete walls will be appropriately called out, identified, measured, or otherwise made understandable by the corresponding indicia formed on the radiographic film.

A target may have location indicia in many forms. Traditional targets for target shooting typically have concentric circles or circular zones for providing visual indication of the very center of the target. A radiographic target according to the present invention may have for example a series of unique location indicia such as a progression of alphabetical letters or of numbers arranged in a circle or in plural concentric circles in the manner of numbers representing hours on the face of a clock. These location indicia may be radially arranged from the center of the target, as is typical of clock faces for example. Alternatively, the location indicia may be radially arranged from a central point which is not located in the center of the target. One example is a square target wherein the central point is located at the very corner of the square. This example is appropriate for targets to be placed at the inside corner of concrete structures forming an inside corner, such as two concrete walls coming together to form a right angle.

According to a further aspect of the invention, the invention may comprise a radiographic image in fixed form such as a radiographic film or paper reproduction generated using the radiographic film, which was made using a target bearing location indicia, which radiographic image in fixed form shows the interior of a concrete structure but which lacks any showing of an inclusion in the concrete. This may be necessary for example to confirm that in a particular portion of a concrete structure, the concrete is solid and uninterrupted by an inclusion, so that that area may be core drilled safely. Alternatively, it may be necessary or desirable merely to confirm that the subject concrete structure is solid and therefore may be regarded as having certain strength properties.

It is an object of the invention to provide improved elements and arrangements thereof by apparatus for the purposes described which is inexpensive, dependable, and fully effective in accomplishing its intended purposes.

These and other objects of the present invention will become readily apparent upon further review of the following specification and drawings.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION

The present disclosure is related to U.S. Pat. No. 7,602,884, issued on Oct. 13, 2009, Ser. No. 12/136,245, filed on Jun. 10, 2008, and hereby incorporates the same in its entirety by reference.

Figure 1:
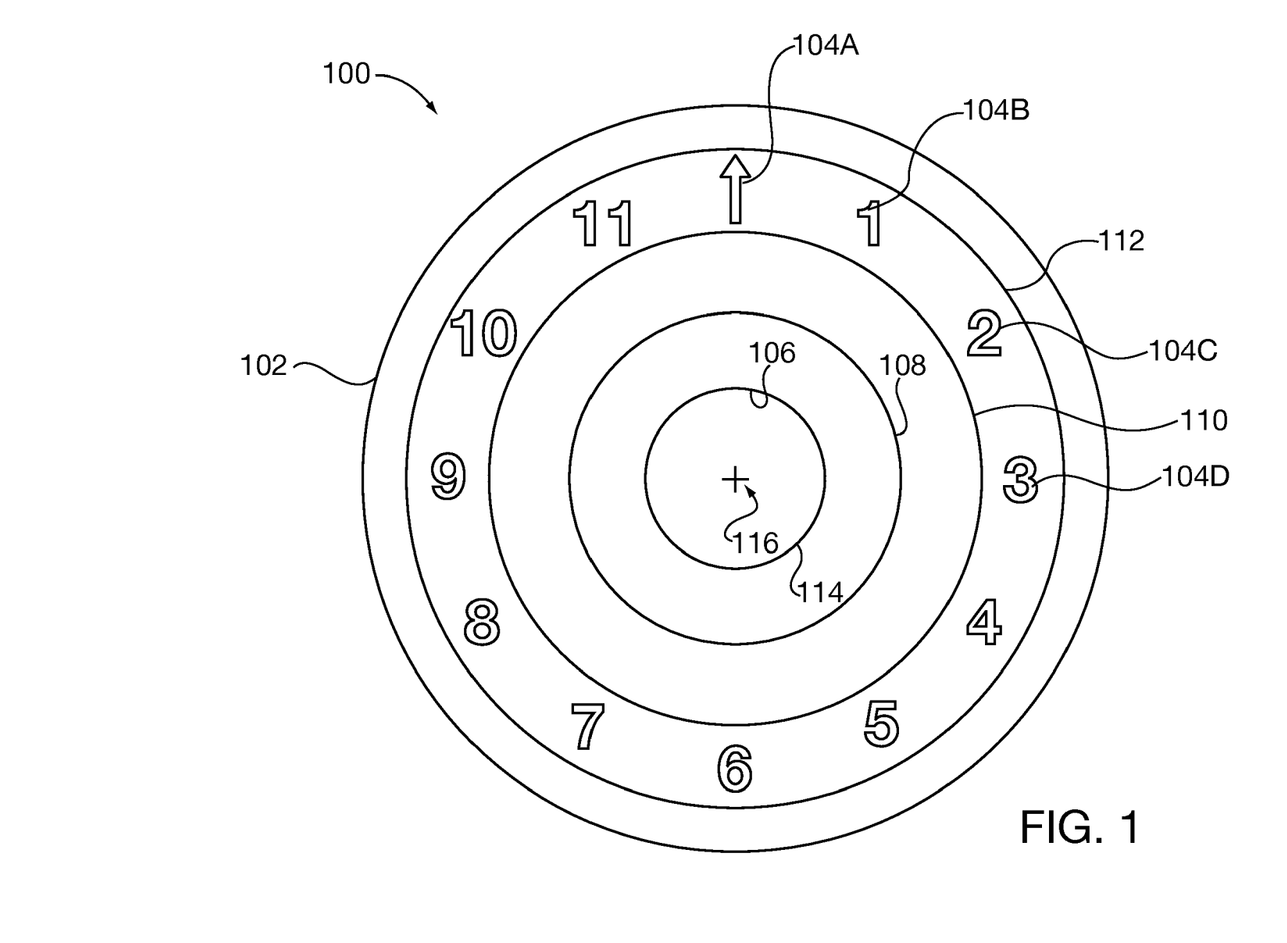
FIG. 1 is a top plan view of a target for imposing indicia onto a radiographic image, according to at least one aspect of the invention.

FIG. 1 shows a target 100 for forming guidance indicia on a radiographic image of an inclusion contained within a substrate, simultaneously with exposing radiographic film to form the radiographic image. For the purposes of this invention, a target such as the target 100 is a device for forming guidance indicia on a radiographic image (an exemplary radiographic image is presented hereinafter) of an inclusion contained within a substrate. The guidance indicia are formed simultaneously with exposing radiographic film to form the radiographic image. Thus internal characteristics of the substrate, such as an inclusion or anomalies, or alternatively, lack of an inclusion and anomalies and the guidance indicia are formed in one film exposure operation on the same image.

By way of summary, concrete radiography relies on radiated energy such as X-rays to generate images on a film, and may be conducted using a source of radiographic energy, which may be for example any known projector of X-rays, and a radiographic film. The film is placed on one side of a concrete structure and the energy is discharged from the opposite side of the concrete structure against the radiographic film. This will produce images of the interior of the concrete structure such that inclusions and other anomalies in what would otherwise be solid concrete are discernible in the final image. An inclusion may be a structural element, such as rebar, post tensioning cables, and internal conduits, embedded energy cables such as electric wires and optic fibers, anchoring elements such as anchor bolts and threaded sockets embedded within the concrete, and others. Anomalies may include for example voids or zones within concrete wherein the constituency differs from elsewhere within the concrete structure, or is suspected of deviating from desired constituency or characteristics. The singular and plural forms of the terms inclusion and the term anomaly will be understood to be interchangeable as used herein. Constituency may encompass chemical or other contamination, undesired ratios of cement, sand, gravel, or other usual components of concrete, unidentified objects or substances or both, or a zone wherein concrete has or may be thought to be insufficiently cured, insufficiently hydrated, or otherwise may be suspected of deviating from a desired constituency.

After radiated energy has been discharged through the concrete structure and against the radiographic film, the film may be developed. A first image of the interior of the radiographed concrete structure then results. The developed radiographic film may then be used to generate copies such as paper copies, or may be used to generate digital or other images for storage, transmission to others, enhancement or other digital manipulation, and subsequent reproduction.

The target 100 may comprise a plate 102 of radiographically pervious material which may be a metal such as aluminum for example bearing radiographically impervious masking material which may be a metal such as lead for example for forming guidance indicia 104A, 104B, 104C, 104D on the final radiographic image (shown and described hereinafter). Where employed herein, specifically named metals will be understood to be substantially those metals, and may be alloys thereof. Of course, materials other than aluminum may be utilized, such as plastics, ceramics, wood, fiberglass, and others. The plate may be circular as shown, or alternatively may be square, rectangular, or of any other desired outer perimetric shape. The target 100 may have a window 106 which may be employed to enable an observer (not shown) to ascertain the precise location of the target 100 on a substrate being radiographed. The window 106 formed in the plate 102 extends entirely through the plate 102 to enable environmental details to be seen. For example, where the substrate comprises a concrete slab (not shown), the slab may be marked with paint which may be seen through the window 106 when the target 100 is placed on the slab. This enables subsequent replacement of the target 100 in the same place in successive radiographic imaging operations by using the paint to spot the location of the target 100.

The radiographically impervious masking material is arranged such that at least some of the guidance indicia is arrayed about the perimeter of the target as a series of spaced apart graphic entities. For example, in FIG. 1, indicia 104A may comprise an arrow which could be used to assure similar orientations of the target in successive radiographic imaging operations. Additional indicia 104B, 104C, and 104D may comprise numerical characters (as shown), or alternatively could comprise alphabetical characters, known symbols such as starts and circles, or any other graphic symbol or character. As shown, the indicial 104B . . . 104D are numeric characters arrayed in numerical order. Additional indicia complete a numeric progression. It will be seen that the numeric indicia are arrayed about the perimeter of the plate 102 and are spaced apart at regular intervals.

Additional indicia in the form of concentric rings 108, 110, and 112 may be provided, and may be centered about the window 106.

Where it is desired that indicia such as the indicia 104A, 104B, 104C, 104D, 108, 110, 112 be discernible in developed radiogrpahic film, then such indicia may comprise radiographically impervious masking material which may fill grooves formed in the plate 102 or passages passing entirely through the plate 102.

The window 106 may have at least one radiographically impervious perimetric visual boundary element 114 which concentrically surrounds the window 106 so as to cause corresponding perimetric indicia surrounding the window 106 to appear on the final radiological image. The visual boundary element 114 may be a groove filled with lead for example. Indicia such as the indicia 104A, 104B, 104C, 104D, 108, 110, and 112 may be generally arrayed in radial symmetry from the center point 116. Of course, because there is no constituent material present at the center point 116 due to the window 106, the center point 116 will be understood to be hypothetical.

Figure 2:
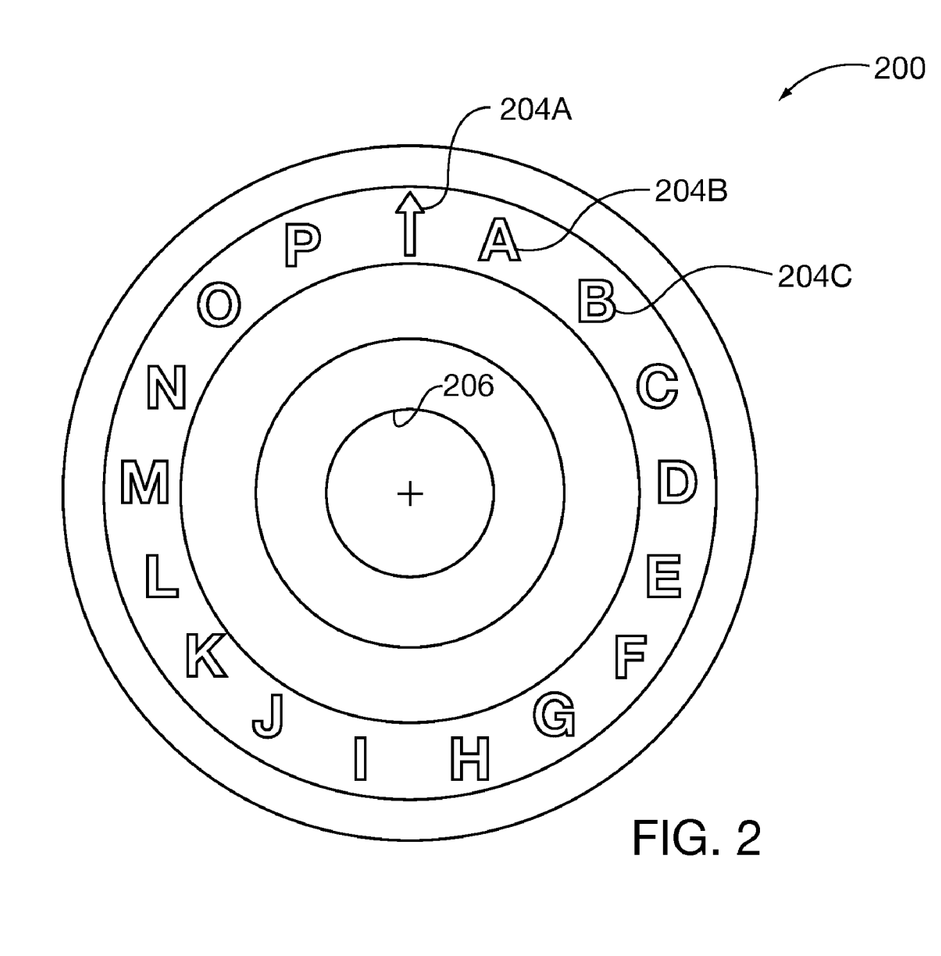
FIG. 2 is an environmental top plan view of a target for imposing indicia onto a radiographic image, according to at least one additional aspect of the invention.

As seen in FIG. 2, a target 200 which may in other ways be the structural and functional similar to the target 100 may have indicia 204B, 204C, and others in the form of alphabetical characters. The target 200 may have indicia comprising an arrow 204A and a window 206. Numerals and alphabetical characters may both appear on a target (not shown) according to other aspects of the invention.

In the targets 100 and 200, guidance indicia such as the guidance indicia 104B, 104C, 204B, 204C are disposed in radial symmetry about the center of the target (such as the point 116 in FIG. 1).

Figure 3:
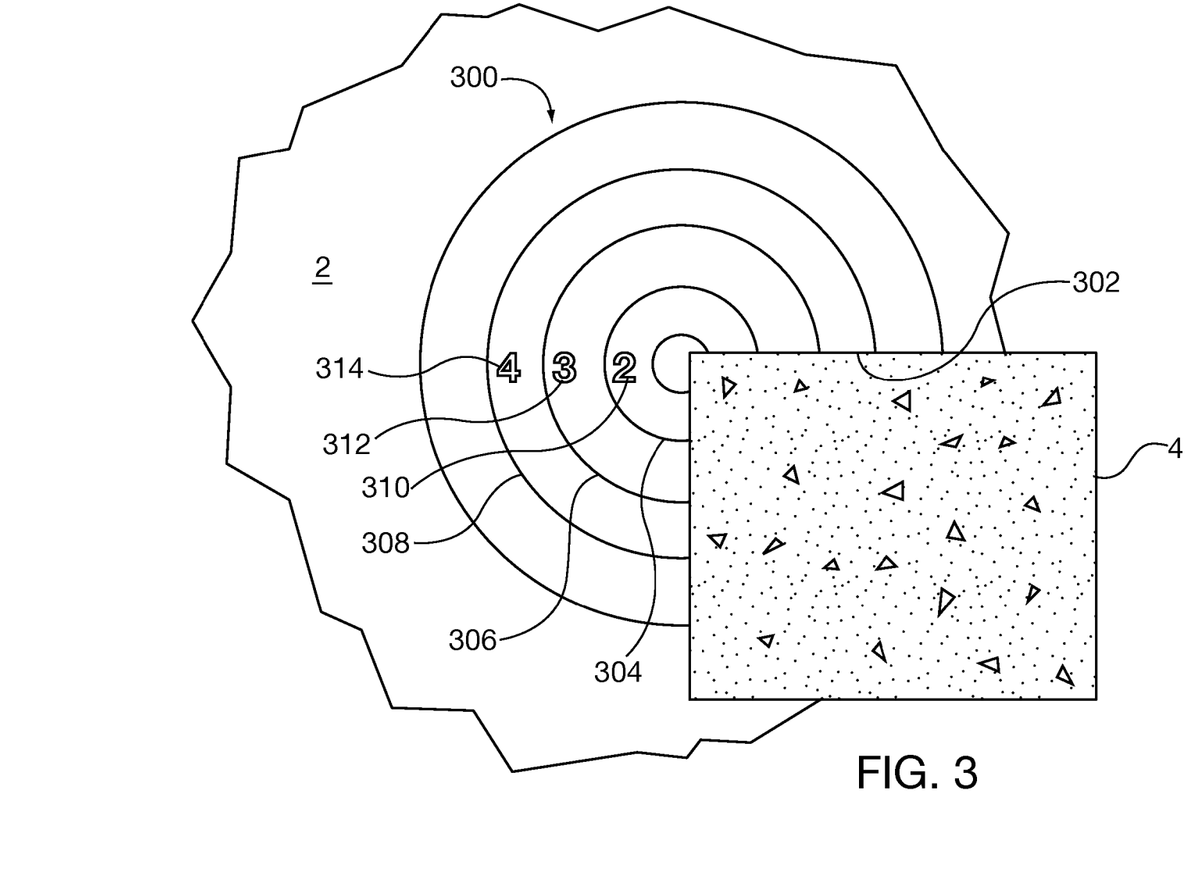
FIG. 3 is an environmental top plan view of a target for imposing indicia onto a radiographic image, according to at least one further aspect of the invention.

The targets 100 and 200 are suitable for laying on or against unobstructed concrete surfaces. It may be desirable that a target be placed where an immovable obstruction exists. Turning now to FIG. 3, a target 300 may be placed on a concrete slab 2 which is the subject of radiographic imagery in abutment with a concrete column 4 which may project from the slab 2. The target 300 may have constituency similar to that of the target 100. The target 300 may have a recess 302 which cooperates with the column 4. In this example, the center of the target 300 may comprise a partially circular portion 304 which is cut out from the constituent material of the target 300 so that a window will remain after the target 300 has been placed in abutment against the column 4.

Unlike the target 100, wherein indicia is generally arrayed in radial symmetry from the center point 116, indicia of the target 300 may be disposed asymmetrically about a hypothetical center point of the target (the hypothetic center point is not shown). It will be appreciated that due to a quadrant of the otherwise circular target 300 being omitted from the target 300 to achieve the configuration which enables the target 300 to be placed snugly against the column 4, the center point of the concentric arcs which form guidance indicia members 304, 306, 308 is not the same as the actual center point of the target 300. Therefore, the indicia, including the guidance indicia members 304, 306, 308 as well as numeric guidance indicia members 310, 312, and 314, are asymmetrically disposed about the hypothetical actual geometric center point of the target 300.

Figure 4:
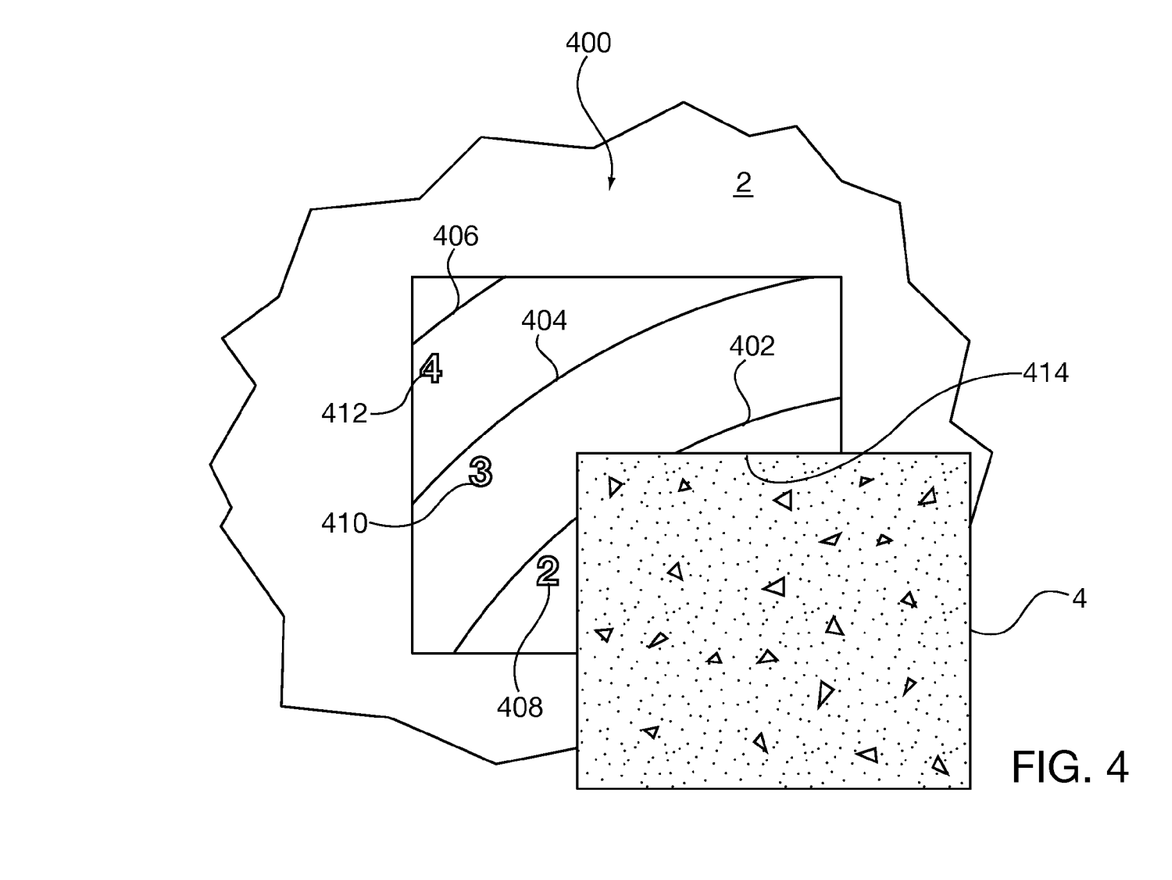
FIG. 4 is an environmental top plan view of a target for imposing indicia onto a radiographic image, according to yet another aspect of the invention.
Figure 5:
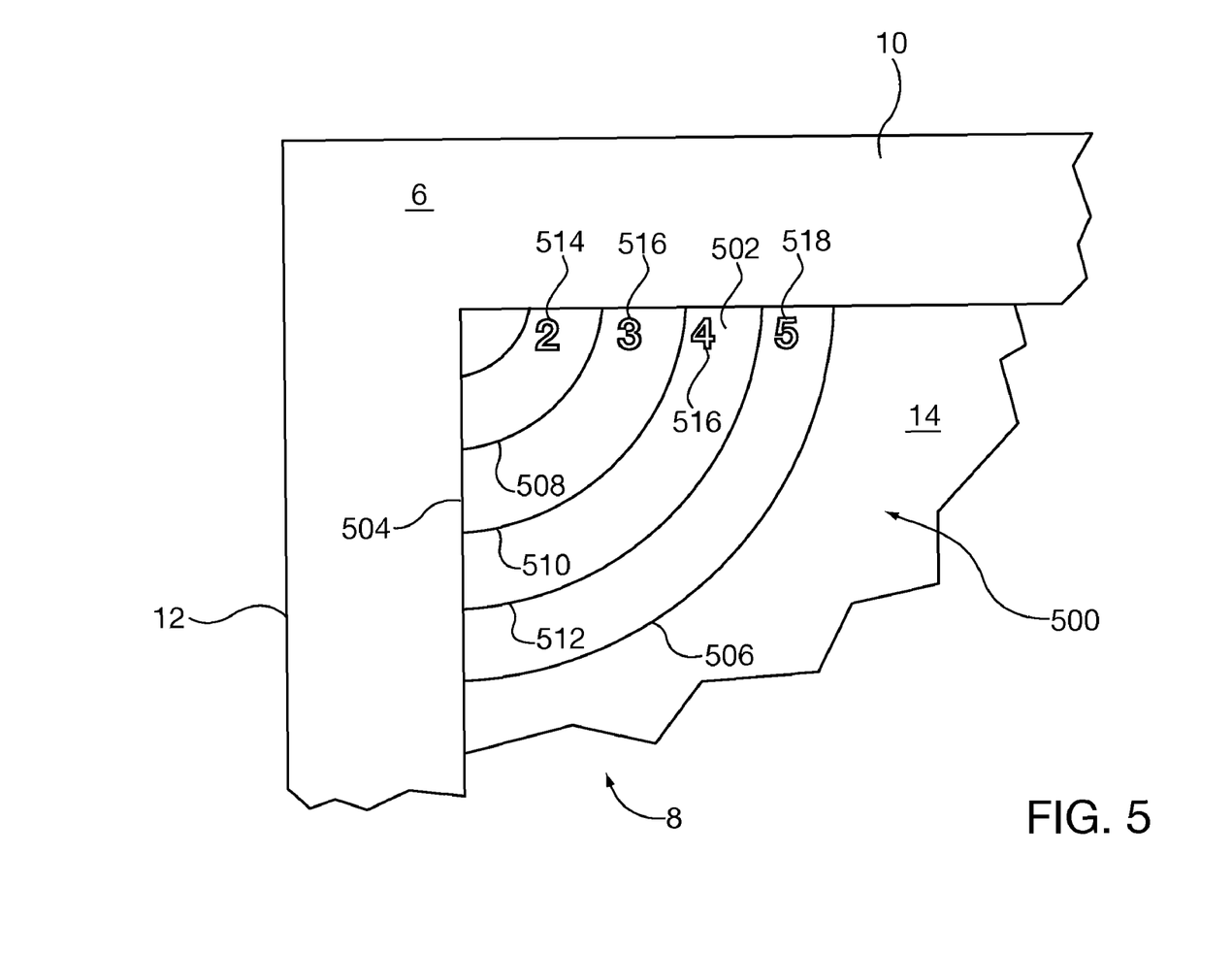
FIG. 5 is an environmental top plan view of a target for imposing indicia onto a radiographic image, according to yet further aspect of the invention.

This relationship may be better appreciated in FIG. 4, wherein a target 400 having an overall L-shaped exterior perimetric configuration is placed against the column 4 in the same position as the target 300 is seen in FIG. 3. The target 400, apart from its L-shaped outer configuration and layout of guidance indicia 402, 404, 406, 408, 410, and 412, may be structurally and functionally similar to the target 100 for example. The guidance indicia 402, 404, and 406 may take the form of arcs radiating from a hypothetic geometric point which lies outside the outer boundaries of the target 400. The guidance indicia 408, 410, and 412 may comprise numeric characters as shown, or may be alphabetical or still other characters.

The targets 300 and 400, which are intended to partially surround the exterior of corners formed on a concrete structure must have perimeters bearing an incuse portion such as the recess 302 in FIG. 3 and a corresponding recess 414 in FIG. 4 to receive the exterior of the concrete structure. The respective recesses 302 and 414 comprise a right angle projecting into the respective targets 300, 400. Of course, a recess such as the recesses 302 and 414 could be of different angles, or could have configurations other than those comprising two straight edges.

Figure 6:
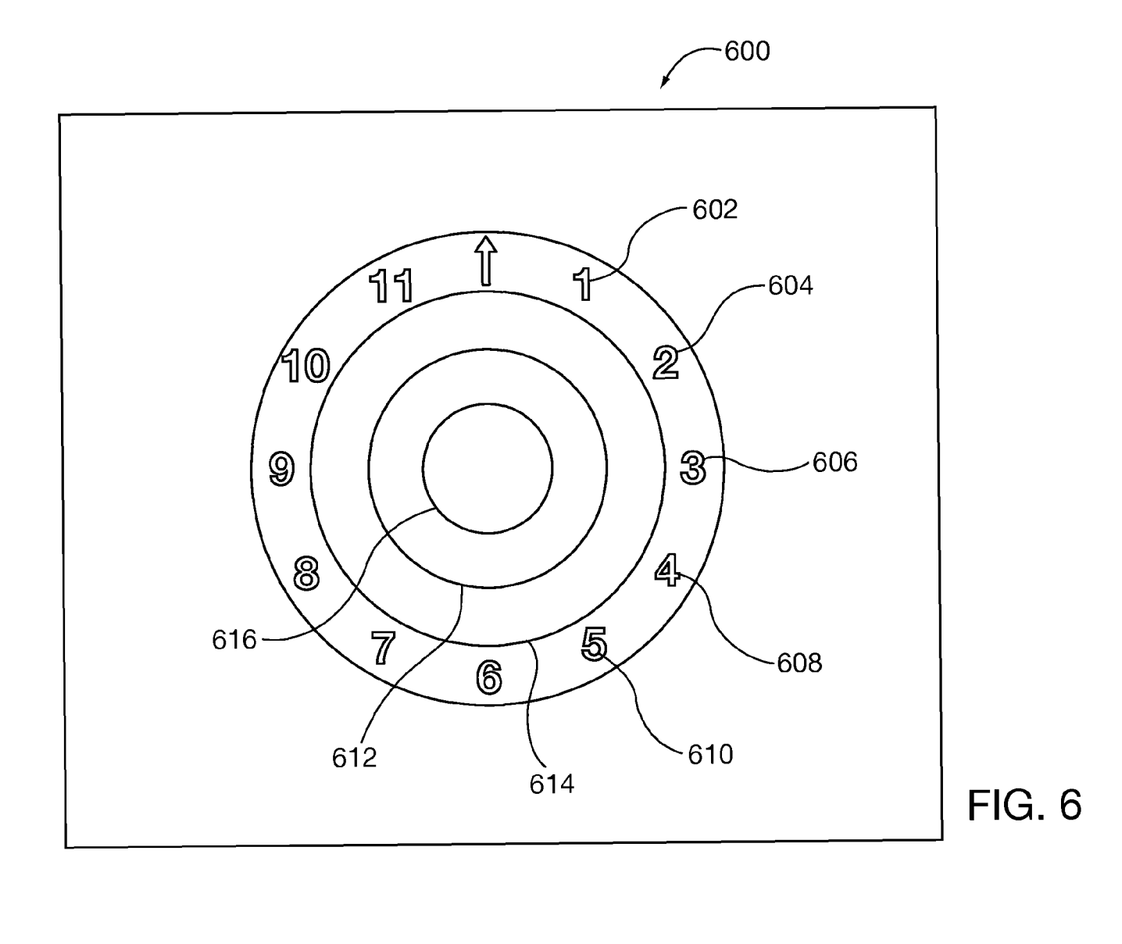
FIG. 6 is an environmental top plan view of a target for imposing indicia onto a radiographic image, according to yet further aspect of the invention.
Figure 7:
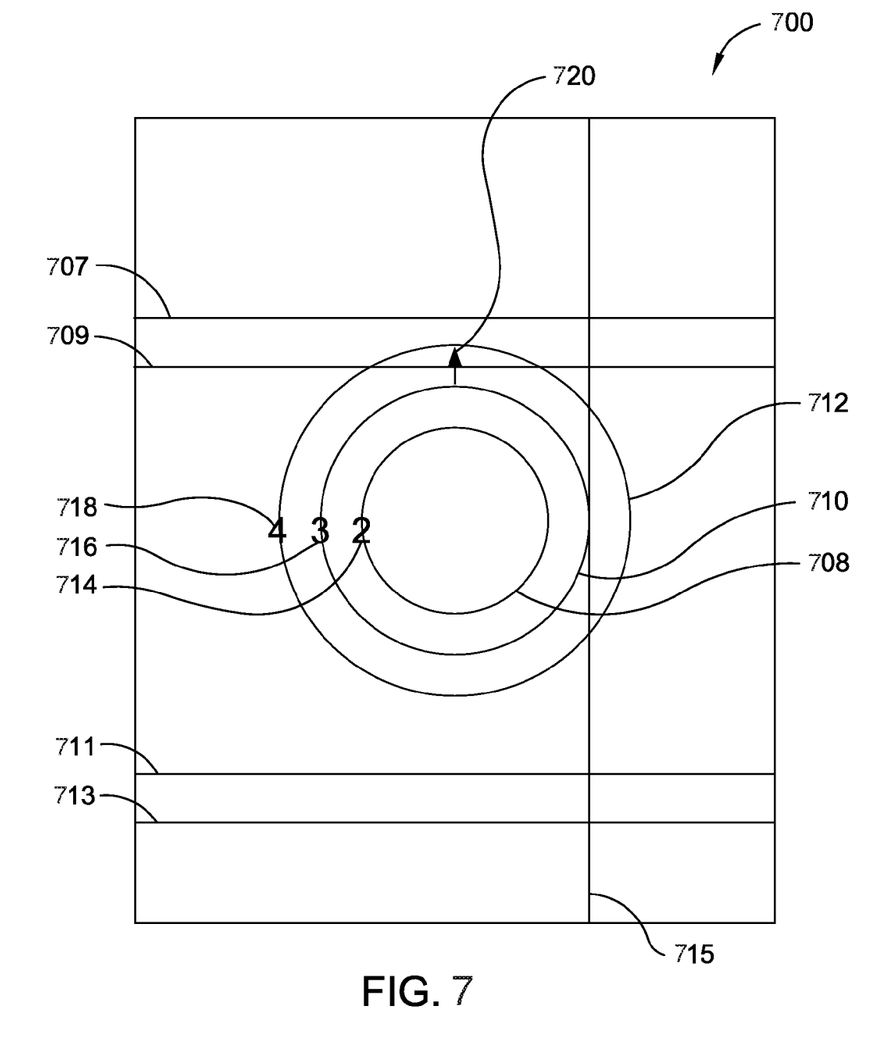
FIG. 7 is an environmental top plan view of a target for imposing indicia onto a radiographic image, according to yet further aspect of the invention.

FIG. 6 shows an image display 600 displaying an image of internal characteristics of a concrete structure, such as a concrete slab (not shown). The image display may take the form of a stratum bearing a radiographic image of the interior of the concrete slab. The image display may be a developed radiographic film, a print made therefrom, a slide made therefrom, or other substrate bearing the radiographic image which has been formed by radiographic imagery of concrete. The radiographic image formed on the image display 600 includes a plurality of indexing marks such as numeric characters 602, 604, 606, 608, 610 and others (not called out by reference numerals). Additional location or guidance indicia such as concentric circles 612, 614, 616 are included in the image. Of course, the indexing marks could be alphabetical characters had the radiographic image used the target 200 for example. These indexing marks are arrayed spaced apart at regular spacing intervals. The indexing marks are derived from use of both a relatively X-ray permeable medium and a relatively X-ray impermeable masking medium, such that different degrees of permeability to X-rays generates on the image display discernible indicia corresponding to the indexing marks. For example, the target 100 may be utilized to generate an image such as that appearing on the image display 600, so that the lead filled concentric rings 108, 110, 112 and indicia characters 104A, 104B, 104C, 104D and others corresponding to lead filled indicia characters are formed on radiographic film due to selective obstruction of X-rays.

The radiographic image of the concrete structure and the indexing marks 602, 604, 606, 608, 610 may be formed in one film exposure operation on the same image by placement of a target such as the target 100 against the concrete structure being radiographed. The internal characteristics of the concrete, such as inclusions (none appear in the image of FIG. 6) and the indexing marks 602, 604, 606, 608, 610 are simultaneously produced on the radiographic film.

It will be seen that while the guidance indicia such as the indexing marks 602, 604, 606, 608, 610 are captured in the image of the image display 600, there are no showings corresponding to inclusions. This confirms that in that portion of the concrete structure which was radiographed to produce the image display 600, no inclusions are present. This information may be used for example to establish integrity of the radiographed concrete structure, or to confirm that a hole may be safely drilled through that portion of the radiographed concrete structure.

I claim:

1. A circular target for forming guidance indicia on a radiographic image of an inclusion contained within a substrate, simultaneously with exposing radiographic film to form the radiographic image, comprising:
   a plate of radiographically pervious material bearing radiographically impervious masking material for forming the guidance indicia on the final radiographic image; and
   means for enabling an observer to ascertain the precise location of the target on the substrate, wherein
   the radiographically impervious masking material is arranged such that at least some of the guidance indicia is arrayed about the perimeter of the target as a series of spaced apart graphic entities.

2. The target according to claim 1, wherein the graphic entities formed as those members of the guidance indicia which are arrayed about the perimeter are spaced apart at regular intervals.

3. The target according to claim 1, wherein the plate is fabricated from a material which is substantially aluminum in composition and the masking material is substantially lead in composition.

4. The target according to claim 1, wherein the means for enabling an observer to ascertain the precise location of the target on the substrate comprises a window formed in and extending entirely through the plate.

5. The target according to claim 4, wherein the means for enabling an observer to ascertain the precise location of the target on the substrate comprises a window formed in and extending entirely through the plate, and wherein the plate has formed therein at least one radiographically impervious perimetric visual boundary element which concentrically surrounds the window so as to cause corresponding perimetric indicia surrounding the window to appear on the final radiological image.

6. The target according to claim 1, wherein the indexing marks comprise at least one of the group including numerals and alphabetical characters.

7. The target according to claim 1, wherein the guidance indicia are disposed asymmetrically about the center of the target.

8. The target according to claim 7, wherein the perimeter of the target comprises a portion forming an angle including a first straight leg and a second straight leg which intersects the first straight leg at a point and terminates at the point.

9. The target according to claim 1, wherein the guidance indicia are disposed asymmetrically about a hypothetical geometric center point of the target.

10. The target according to claim 9, wherein the guidance indicia are arrayed in radial symmetry from a hypothetical geometric reference point located on the perimeter of the target.

11. A target for forming guidance indicia on a radiographic image of an inclusion contained within a substrate, simultaneously with exposing radiographic film to form the radiographic image, comprising a plate of radiographically pervious material bearing radiographically impervious masking material for forming guidance indicia on the final radiographic image, wherein the plate of radiographically pervious material has a perimeter bearing an incuse portion.

12. The target according to claim 11, wherein the incuse portion comprises a right angle projecting into the target.

13. The target according to claim 12, wherein the target has an overall L-shaped exterior perimetric configuration.

14. A target for forming guidance indicia on a radiographic image of an inclusion contained within a substrate, simultaneously with exposing radiographic film to form the radiographic image, comprising
   a plate of radiographically pervious material fabricated from metal bearing radiographically impervious masking material fabricated from another metal for forming the guidance indicia on the final radiographic image; and
   means for enabling an observer to ascertain the precise location of the target on the substrate, wherein
   the radiographically impervious masking material is arranged such that at least some of the guidance indicia is arrayed about the perimeter of the target as a series of spaced apart graphic entities.

15. The target according to claim 14, wherein the graphic entities formed as those members of the guidance indicia which are arrayed about the perimeter are spaced apart at regular intervals.

16. The target according to claim 14, wherein the means for enabling an observer to ascertain the precise location of the target on the substrate comprises a window formed in and extending entirely through the plate.

17. The target according to claim 16, wherein the means for enabling an observer to ascertain the precise location of the target on the substrate comprises a window formed in and extending entirely through the plate, and wherein the plate has formed therein at least one radiographically impervious perimetric visual boundary element which concentrically surrounds the window so as to cause corresponding perimetric indicia surrounding the window to appear on the final radiological image.

18. The target according to claim 14, wherein the indexing marks comprise at least one of the group including numerals and alphabetical characters.

19. The target according to claim 14, wherein the guidance indicia are disposed asymmetrically about the center of the target.

20. The target according to claim 14, wherein the guidance indicia are disposed asymmetrically about a hypothetical geometric center point of the target.

* * * * *